United States Patent
Umehara et al.

(10) Patent No.: US 6,890,457 B2
(45) Date of Patent: May 10, 2005

(54) ADHESIVE

(75) Inventors: Katsuhiko Umehara, Shizuoka-ken (JP); Toshiyuki Waragai, 702-30, Shimotogari, Nagaizumi-cho, Sunto-gun, Shizuoka-ken (JP)

(73) Assignee: Toshiyuki Waragai, Shizuoka-ken (JP)

( * ) Notice: Subject to any disclaimer, the term of this patent is extended or adjusted under 35 U.S.C. 154(b) by 54 days.

(21) Appl. No.: 10/340,921

(22) Filed: Jan. 14, 2003

(65) Prior Publication Data

US 2004/0056240 A1 Mar. 25, 2004

(51) Int. Cl.$^7$ .............................. C09K 3/00; C09J 11/04; C09J 131/04; C09J 157/00; A61K 51/06

(52) U.S. Cl. ................. 252/625; 252/644; 252/645; 252/646; 523/218; 523/220; 524/430; 524/431; 524/433; 524/439; 524/440; 427/5; 424/1.11; 424/1.29

(58) Field of Search ................. 523/218, 220; 524/430, 431, 433, 439, 440; 252/625, 644, 645, 646; 424/1.11, 1.29; 427/5; 368/226

(56) References Cited

U.S. PATENT DOCUMENTS

| | | | | |
|---|---|---|---|---|
| 1,461,340 A | * | 7/1923 | Adams ........................ 504/187 |
| 1,645,599 A | * | 10/1927 | Jones ............................ 600/1 |
| 3,431,721 A | * | 3/1969 | Slaugh ........................ 368/226 |
| 3,772,200 A | * | 11/1973 | Livesay ....................... 252/645 |
| 4,360,611 A | * | 11/1982 | Wakimoto et al. .......... 523/216 |
| 4,965,434 A | * | 10/1990 | Nomura et al. .............. 392/407 |
| 5,030,510 A | * | 7/1991 | Yokoyama et al. ....... 428/305.5 |
| 5,234,985 A | * | 8/1993 | Koo et al. .................... 524/492 |
| 5,419,855 A | * | 5/1995 | Kikuta ......................... 252/587 |
| 6,004,588 A | * | 12/1999 | Torii et al. ................... 424/682 |
| 6,198,212 B1 | * | 3/2001 | Kim et al. ................... 313/479 |
| 6,402,991 B1 | * | 6/2002 | Itakura et al. ............... 252/500 |
| 6,597,004 B2 | * | 7/2003 | Imai ........................ 250/493.1 |
| 2002/0139963 A1 | * | 10/2002 | Kim ............................ 252/582 |
| 2004/0060141 A1 | * | 4/2004 | Kim ........................... 15/159.1 |

FOREIGN PATENT DOCUMENTS

| | | | | |
|---|---|---|---|---|
| EP | 433097 A1 | * | 6/1991 | ............ C08K/3/22 |
| JP | 52150366 A | * | 12/1977 | .............. B01J/1/00 |
| JP | 58034875 A | * | 3/1983 | .............. C09J/3/00 |
| JP | 60155267 A | * | 8/1985 | ......... C08L/101/00 |
| JP | 02001781 A | * | 1/1990 | ............ C09J/11/00 |
| JP | 02101003 A | * | 4/1990 | .......... A01N/25/34 |
| JP | 02135265 A | * | 5/1990 | ............ C09D/5/00 |
| JP | 02295733 A | * | 12/1990 | ........... B32B/15/08 |
| JP | 08141505 A | * | 6/1996 | ............. B05D/7/24 |
| JP | 2000128621 A | * | 5/2000 | ........... C04B/35/00 |
| JP | 2000219858 A | * | 8/2000 | ............ C09J/11/04 |
| JP | 2001200233 A | * | 7/2001 | .......... C09J/201/00 |
| JP | 2002112812 A | * | 4/2002 | ............. A44C/9/00 |
| JP | 2003342479 A | * | 12/2003 | ......... C08L/101/00 |
| WO | WO 00/34411a1 | * | 6/2000 | ........... C09K/11/08 |

OTHER PUBLICATIONS

Derwent abstract (ACC–NO 2002–448762) for JP2002 112812–A (Apr. 16, 2002) Satoyoshi.*

(Continued)

*Primary Examiner*—Matthew A. Thexton
(74) *Attorney, Agent, or Firm*—Harrison & Egbert

(57) ABSTRACT

An adhesive containing a far infrared radiation ceramic powder emitting far infrared rays and a radiation source ceramic powder emitting radiations and anions. The radiation source ceramic powder includes silicon dioxide, aluminum oxide, iron oxide, titanium oxide, calcium oxide, magnesium oxide, potassium oxide, sodium oxide and zirconium and/or radium. The adhesive according to the present invention relaxes human beings, helps spontaneous recovery from diseases and improves health by the synergistic effects of far infrared rays, anions and radiations.

5 Claims, 1 Drawing Sheet

OTHER PUBLICATIONS

JPO abstract for JP 2001200233 A (Jul. 24, 2001), Umehara et al.*
JPO abstract for JP 2000 219858 A (Aug. 8, 2000), Umehara et al.*
JPO machine translation of JP08–141505–A.*
Derwent machine assisted translation of JP2000–219858–A.*
Derwent machine assisted translation of JP2001–200233–A.*
Derwent abstract ACC–NO: 1983–33640K (for JP 58–034875–A).*
Derwent abstract ACC–NO: 1985–239417 (for JP 60–155267–A).*
JPO abstract for JP 2–295733–A.*
Derwent abstract ACC–NO: 1973–20993U (for JP 73011026–B).*
Derwent abstract ACC–NO: 1978–08950A (for JP 52–150366–A).*
Derwent abstract ACC–NO: 1990–048380 (for JP 2–001781–A).*
Derwent abstract ACC–NO: 1990–159743 (for JP 2–101003–A).*
Derwent abstract ACC–NO: 1990–204924 (for JP 2–135265–A).*
JPO abstract for JP 2003–342479–A.*
Derwent abstract ACC–NO: 2004–140648 (for KR 2003–079902–A).*

* cited by examiner

ADHESIVE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to an adhesive.

The adhesive of the present invention is used, for example, for adhesion between wooden members, between paper members, between leather members, between metallic members, between rubber members, between plastic members, or between ceramic members, or for adhesion between one of these members and another of these members of different materials.

The adhesive of the present invention is used also for sticking plywood members, laminate lumber members, wall covering, flooring, artificial lawn, ceramic members, etc. to ground materials.

BACKGROUND OF THE INVENTION

The inventors of the present invention already provided adhesives disclosed by Japanese Patent Laid-Open Publications No. 2000-219858 and No. 2001-200233. These adhesives comprise a basic adhesive such as a vinyl acetate resin emulsion-type adhesive, said basic adhesive being mixed with a far infrared radiation ceramic powder emitting far infrared rays, an absorption/decomposition ceramic powder, an antibacterial ceramic powder, hollow ceramic balls, etc.

Said far infrared radiation ceramic powder contained in the adhesives of the prior art emits far infrared rays which relax human beings.

Said absorption/decomposition ceramic powder contained in the adhesives of the prior art absorbs or decomposes harmful chemical substances in the adhesives so as to eliminate bad influences on human beings and bad or irritating smells.

Said antibacterial ceramic powder contained in the adhesives of the prior art makes an antibacterial action against molds, *Bacillus coll, Staphylococcus aureus, Bacillus pyocyaneus, Candida bacillus, Streptococcus mutans*, etc.

Said hollow ceramic balls are contained in adhesives for wallpaper. The hollow ceramic balls are dispersed in the adhesives so as to adjust the temperature and humidity in the building.

BRIEF SUMMARY OF THE INVENTION

It is an object of the invention to provide an adhesive which has an anion effect and a radiation hormesis effect synergistically in addition to said relaxation effect by said far infrared radiation ceramic powder contained in the adhesives of the prior art.

It is another object of the invention to provide an adhesive which helps spontaneous recovery from diseases and improves health.

These and other objects have been attained by an adhesive containing a far infrared radiation ceramic powder emitting far infrared rays and a radiation source ceramic powder emitting radiations and anions.

Said radiation source ceramic powder comprises silicon dioxide, aluminum oxide, iron oxide, titanium oxide, calcium oxide, magnesium oxide, potassium oxide, sodium oxide and zirconium.

Alternatively, said radiation source ceramic powder may comprise silicon dioxide, aluminum oxide, iron oxide, titanium oxide, calcium oxide, magnesium oxide, potassium oxide, sodium oxide and radium.

Or, said radiation source ceramic powder may comprise silicon dioxide, aluminum oxide, iron oxide, titanium oxide, calcium oxide, magnesium oxide, potassium oxide, sodium oxide, zirconium and radium.

The adhesives of the present invention include an adhesive containing at least one of said absorption/decomposition ceramic powder, antibacterial ceramic powder and hollow ceramic balls. Also, the adhesives of the present invention include an adhesive containing none of said absorption/decomposition ceramic powder, antibacterial ceramic powder and hollow ceramic balls.

The iron oxide in the claims and specification includes iron sesquioxide ($Fe_2O_3$).

Said far infrared radiation ceramic powder contained in the adhesive relaxes human beings by emitting far infrared rays having a wavelength of 9 to 10 $\mu$m. Also, said infrared radiation ceramic powder contained in the adhesive help animals and plants to grow by emitting far infrared rays having a wavelength of 4 to 14 $\mu$m.

Said radiation source ceramic powder contained in the adhesive purifies the blood, balances the autonomic nerve and relieves fatigue by emitting anions. The radiation source ceramic powder emits anions when the ceramic powder is at a standstill or is vibrated or abraded. The radiation source ceramic powder may be natural ores reduced to powder or artificially formed.

Said radiation source ceramic powder contained in the adhesive emits radiations in small doses. Radiations in small doses have a hormesis effect (radiation hormesis). Radiations in small doses are said to exert a favorable influence on the human body and help spontaneous recovery from diseases. Hormesis is a phenomenon that harmful substances in harmless quantity cause stimulative reactions in living things.

The adhesive according to the present invention relaxes human beings, helps spontaneous recovery from diseases and improves health by the synergistic effects of said far infrared rays, anions and radiations.

DETAILED DESCRIPTION OF THE INVENTION

Figure 1:
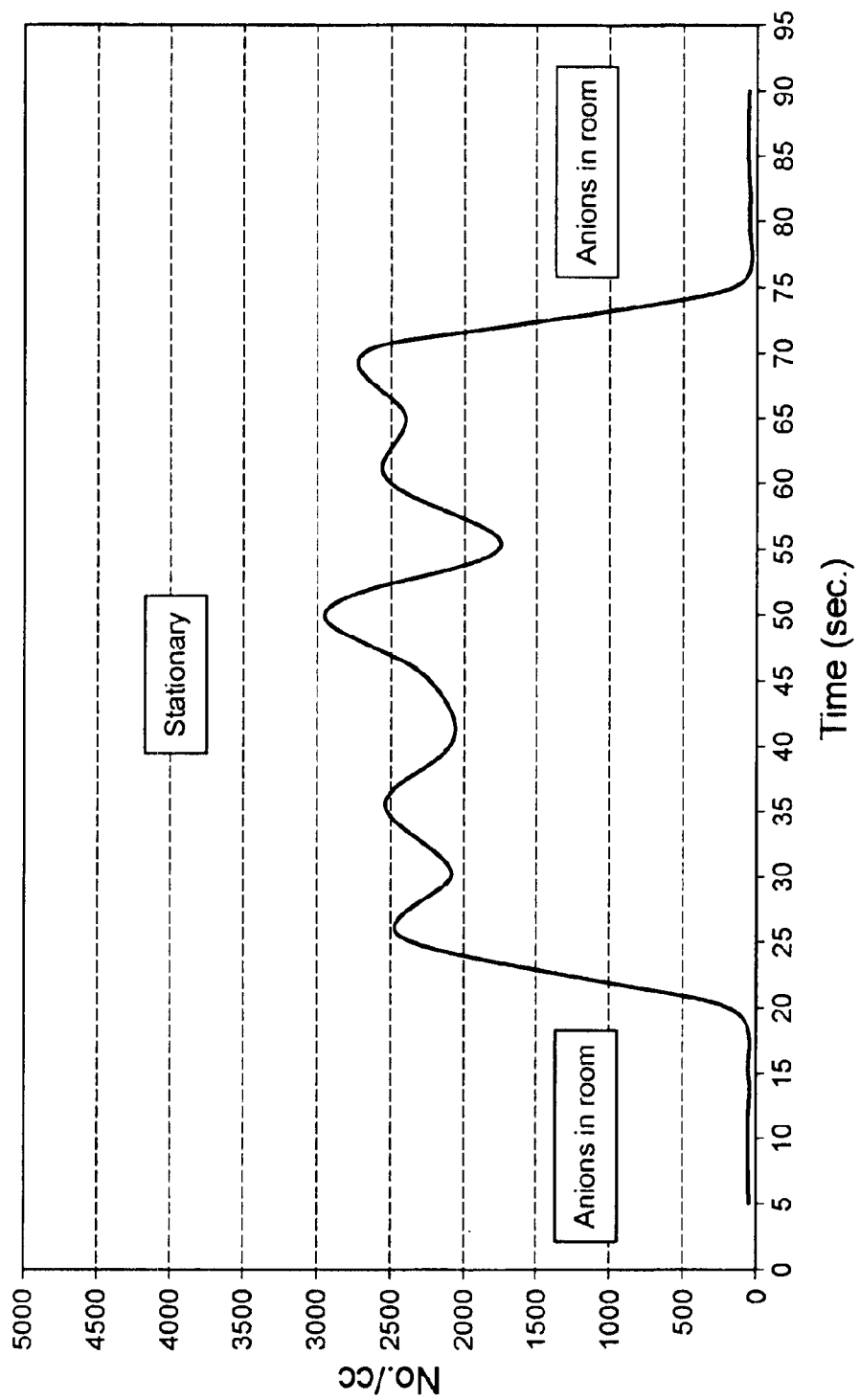
FIG. 1 is a graphical representation showing the quantities of anions emitted by a radiation source ceramic powder.

The present invention will now be described in detail.

The adhesive of the present invention contains a far infrared radiation ceramic powder emitting far infrared rays and a radiation source ceramic powder emitting radiations and anions.

Said adhesive may contain at least one of an absorption/decomposition ceramic powder, an antibacterial ceramic powder and hollow ceramic balls, in addition to said far infrared radiation ceramic powder and said radiation source ceramic powder.

A basic adhesive, to which said ceramic powders, etc. are added, may be, for example, a vinyl acetate resin emulsion-type adhesive or a vinyl copolymer resin emulsion-type adhesive.

Said radiation source ceramic powder comprises, for example, silicon dioxide ($SiO_2$), aluminum oxide ($A_2O_3$), iron sesquioxide ($Fe_2O_3$), titanium oxide ($TiO_2$), calcium oxide (CaO), magnesium oxide (MgO), potassium oxide ($K_2O$), sodium oxide ($Na_2O$) and zirconium (Zr), the percentages by weight thereof being as follows, for example.

| | |
|---|---|
| silicon dioxide: | 66.04% |
| aluminum oxide: | 19.05% |
| iron sesquioxide: | 0.29% |
| titanium oxide: | 0.03% |
| calcium oxide: | 0.52% |
| magnesium oxide: | 0.10% |
| potassium oxide: | 6.41% |
| sodium oxide: | 6.46% |
| zirconium | 0.65% |

The quantities of anions emitted by the radiation source ceramic powder mentioned above were determined as follows.

About 100 cubic centimeters of the radiation source ceramic powder was scattered about 1 centimeter thick on a table. An ion counter was fixed at a height of about 5 centimeters above the table surface. The quantities of anions emitted by the radiation source ceramic powder were determined for 90 seconds by means of the ion counter. The quantities of anions were determined 10 times in this way. The average quantities of anions determined are shown in FIG. 1.

The amount of zirconium is about 0.1 to 20% by weight of the total amount of the radiation source ceramic powder.

Alternatively, said radiation source ceramic powder may comprise silicon dioxide, aluminum oxide, iron oxide, titanium oxide, calcium oxide, magnesium oxide, potassium oxide, sodium oxide and radium.

In this case the amount of radium is about 0.1 to 20% by weight of the total amount of the radiation source ceramic powder.

Or, said radiation source ceramic powder may comprise silicon dioxide, aluminum oxide, iron oxide, titanium oxide, calcium oxide, magnesium oxide, potassium oxide, sodium oxide, zirconium and radium.

In this case the total amount of zirconium and radium is about 0.1 to 20% by weight of the total amount of the radiation source ceramic powder.

The radiation source ceramic powder preferably has a radioactive decay of less than 370 Bq per gram.

Said far infrared radiation ceramic powder emitting far infrared rays has a diameter of about 1 to 44 $\mu$m.

Said radiation source ceramic powder has a diameter of about 1 to 44 $\mu$m.

Said absorption/decomposition ceramic powder has a diameter of about 1 to 44 $\mu$m.

Said antibacterial ceramic powder has a diameter of about 1 to 44 $\mu$m.

Said hollow ceramic balls have a diameter of about 100 $\mu$m.

The adhesive of the present invention is produced as follows. The far infrared radiation ceramic powder and radiation source ceramic powder are put into a container, if necessary along with other ceramic powders mentioned above. Then, a powdered basic adhesive is added to the ceramic powders in the container and these are agitated together.

Some example of the present invention will now be described.

EXAMPLE 1

An adhesive was prepared as follows. 2 parts by weight of a far infrared radiation ceramic powder having a diameter of about 3 to 10 $\mu$m, 3 parts by weight of a radiation source ceramic powder having a diameter of about 3 to 10 $\mu$m, said radiation source ceramic powder containing 3% by weight thereof of zirconium, 3 parts by weight of an absorption/decomposition ceramic powder having a diameter of about 5 to 15 $\mu$m, and 1 part by weight of an antibacterial ceramic powder having a diameter of about 3 to 10 $\mu$m were put into a container. Then, about 300 parts by weight of a powdered basic material of a vinyl acetate resin emulsion-type adhesive was added to the above in the container and these were agitated together.

EXAMPLE 2

An adhesive was prepared as follows. 2 parts by weight of a far infrared radiation ceramic powder having a diameter of about 3 to 10 $\mu$m, 3 parts by weight of a radiation source ceramic powder having a diameter of about 3 to 10 $\mu$m, said radiation source ceramic powder containing 3% by weight thereof of radium, 3 parts by weight of an absorption/decomposition ceramic powder having a diameter of about 5 to 15 $\mu$m, and 1 part by weight of an antibacterial ceramic powder having a diameter of about 3 to 10 $\mu$m were put into a container. Then, about 300 parts by weight of a powdered basic material of a vinyl acetate resin emulsion-type adhesive was added to the above in the container and these were agitated together.

EXAMPLE 3

An adhesive was prepared as follows. 2 parts by weight of a far infrared radiation ceramic powder having a diameter of about 3 to 10 $\mu$m, 3 parts by weight of a radiation source ceramic powder having a diameter of about 3 to 10 $\mu$m, said radiation source ceramic powder containing a total of 3% by weight thereof of zirconium and radium, 3 parts by weight of an absorption/decomposition ceramic powder having a diameter of about 5 to 15 $\mu$m, and 1 part by weight of an antibacterial ceramic powder having a diameter of about 3 to 10 $\mu$m were put into a container. Then, about 300 parts by weight of a powdered basic material of a vinyl acetate resin emulsion-type adhesive was added to the above in the container and these were agitated together.

The present invention has the following advantages.

By the synergistic effects of said far infrared rays, anions and radiations, the adhesive according to the present invention relaxes human beings, helps spontaneous recovery from diseases and improves health. The synergistic effects of said far infrared rays, anions and radiations are not obtained by the adhesives of the prior art mentioned above.

As many apparently widely different examples of the present invention may be made without departing from the spirit and scope thereof, it is to be understood that the invention is not limited to the specific examples thereof except as defined in the appended claims.

We claim:

1. An adhesive composition comprising:
   adhesive material selected from the group consisting of vinyl acetate resin and vinyl copolymer resin;
   a far infrared radiation ceramic powder; and
   a radiation source ceramic powder comprising silicon dioxide, aluminum oxide, iron oxide, titanium oxide, calcium oxide, magnesium oxide, potassium oxide, sodium oxide, and either or both radium and zirconium, wherein the radium and zirconium together are about 0.1 to 20% by weight of the total amount of the radiation source ceramic powder,
   said far infrared radiation ceramic powder and said radiation source ceramic powder being mixed with said adhesive material.

2. The composition of claim 1, said far infrared radiation ceramic powder and said radiation source ceramic powder having powder particles with a diameter of between 1 micrometer and 44 micrometers.

3. The composition of claim 1, said radiation source ceramic powder having a radioactive decay of less than 370 Bq.

4. The composition of claim 1, two parts of said far infrared radiation ceramic powder and three parts of radiation source ceramic powder being mixed with 300 parts of said adhesive material.

5. The composition of claim 1, said adhesive material having hollow ceramic balls therein.

* * * * *